(12) United States Patent
Pfister et al.

(10) Patent No.: US 12,191,033 B2
(45) Date of Patent: Jan. 7, 2025

(54) MONITORING SYSTEM FOR MONITORING A PATIENT AND METHOD FOR OPERATING THE MONITORING SYSTEM

(71) Applicant: Siemens Healthcare GmbH, Erlangen (DE)

(72) Inventors: Marcus Pfister, Bubenreuth (DE); Martin Berger, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 923 days.

(21) Appl. No.: 17/126,000

(22) Filed: Dec. 17, 2020

(65) Prior Publication Data

US 2021/0186339 A1    Jun. 24, 2021

(30) Foreign Application Priority Data

Dec. 19, 2019    (DE) ..................... 10 2019 220 224.1

(51) Int. Cl.
*G16H 20/70* (2018.01)
*A61B 5/00* (2006.01)
(Continued)

(52) U.S. Cl.
CPC ............. *G16H 40/67* (2018.01); *A61B 5/165* (2013.01); *A61B 5/741* (2013.01); *A61M 21/00* (2013.01);
(Continued)

(58) Field of Classification Search
None
See application file for complete search history.

(56) References Cited

U.S. PATENT DOCUMENTS 5,356,287 A    10/1994    Mcintyre
5,676,633 A    10/1997    August
(Continued)

FOREIGN PATENT DOCUMENTS

CN    1886170 A    12/2006
CN    101923669 A    12/2010
(Continued)

OTHER PUBLICATIONS

Arik, Sercan, et al. "Neural voice cloning with a few samples." Advances in Neural Information Processing Systems 31 (2018): 1-18.
(Continued)

*Primary Examiner* — Kyle Zhai
(74) *Attorney, Agent, or Firm* — Lempia Summerfield Katz LLC

(57) ABSTRACT

For particularly good communication even with difficult patients, a monitoring system for monitoring a patient, such as during a medical diagnostic or therapeutic procedure, is provided. The monitoring system includes a voice cloning device having a voice generator. The voice cloning device is configured to replace a natural voice of a person with a cloned synthetic voice different from the voice of the person. At least two synthetic voices may be selected. The monitoring system also includes a measuring unit configured to record at least one physiological parameter of the patient, an evaluation unit configured to evaluate the at least one measured physiological parameter of the patient, and an actuation unit configured to actuate the voice cloning device such that a synthetic voice is selected or rejected depending on a result of the evaluation by the evaluation unit.

15 Claims, 2 Drawing Sheets

(51) Int. Cl.
*A61B 5/16* (2006.01)
*A61M 21/00* (2006.01)
*G06N 20/00* (2019.01)
*G06T 11/00* (2006.01)
*G10L 21/007* (2013.01)
*G16H 40/67* (2018.01)
*G16H 50/30* (2018.01)
*G16H 80/00* (2018.01)

(52) U.S. Cl.
CPC .............. *G06N 20/00* (2019.01); *G06T 11/00* (2013.01); *G10L 21/007* (2013.01); *G16H 20/70* (2018.01); *G16H 50/30* (2018.01); *G16H 80/00* (2018.01); *A61M 2021/0027* (2013.01); *A61M 2021/005* (2013.01)

(56) References Cited

U.S. PATENT DOCUMENTS

| | | | |
|---|---|---|---|
| 5,917,414 A | 6/1999 | Oppelt et al. | |
| 10,827,961 B1* | 11/2020 | Iyengar | A61B 5/1455 |
| 2004/0130449 A1* | 7/2004 | Hung | G08B 21/0208 |
| | | | 340/539.15 |
| 2007/0176920 A1 | 8/2007 | Raijmakers et al. | |
| 2008/0281164 A1 | 11/2008 | Stebor et al. | |
| 2013/0231581 A1 | 9/2013 | Kaellstrand | |
| 2018/0137875 A1* | 5/2018 | Liu | G10L 21/013 |
| 2020/0281532 A1* | 9/2020 | Davis | A61G 11/00 |
| 2020/0410976 A1* | 12/2020 | Zhou | G06N 3/048 |

FOREIGN PATENT DOCUMENTS

| | | |
|---|---|---|
| CN | 102178540 A | 9/2011 |
| CN | 103298398 A | 9/2013 |
| CN | 103996155 A | 8/2014 |
| CN | 204840598 U | 12/2015 |
| CN | 109830304 A | 5/2019 |
| DE | 19637383 A1 | 4/1998 |
| DE | 102004001801 A1 | 7/2005 |
| DE | 102016219157 A1 | 8/2017 |
| DE | 102017220500 A1 | 5/2019 |
| JP | 2009020794 A | 1/2009 |
| JP | 2018121967 A | 8/2018 |
| KR | 20140099569 A | 8/2014 |
| TW | 201801678 A | 1/2018 |
| WO | 2015158017 A1 | 10/2015 |

OTHER PUBLICATIONS

Kietzmann, Jan, et al. "Deepfakes: Trick or treat?. " Business Horizons 63.2 (2020): 135-146.
Samantha Cole "This AI only needs a 3.7-second recording to clone your voice." VICE online magazine, 2018.https://www.vice.com/de/article/3k7mgn/diese-ki-braucht-nur-eine-37-sekunden-lange-aufnahme-dann-klont-sie-eure-stimme.
Solsman, E. J. "Samsung deepfake AI could fabricate a video of you from a single profile pic." (May 2019). pp. 1-6.
Thies, Justus, et al. "Face2face: Real-time face capture and reenactment of rgb videos." Proceedings of the IEEE conference on computer vision and pattern recognition. 2016. pp. 1-9.
Thies, Justus, et al. "Headon: Real-time reenactment of human portrait videos." ACM Transactions on Graphics (TOG) 37.4 (2018): 1-13.

* cited by examiner

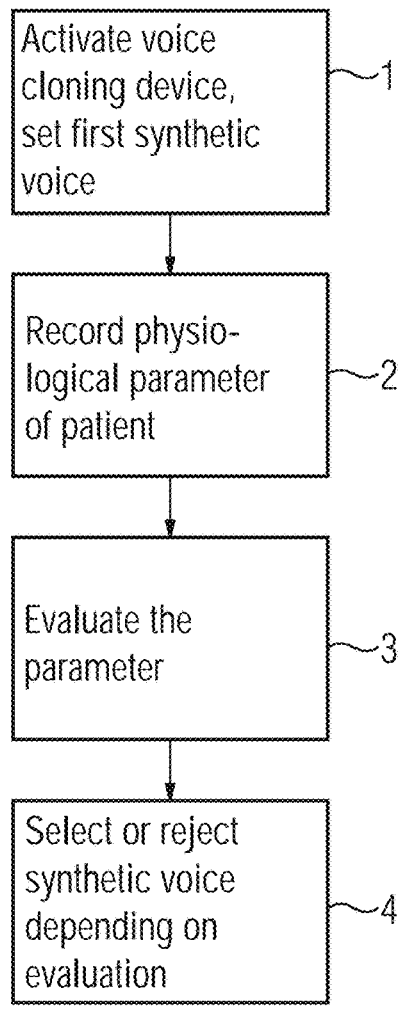
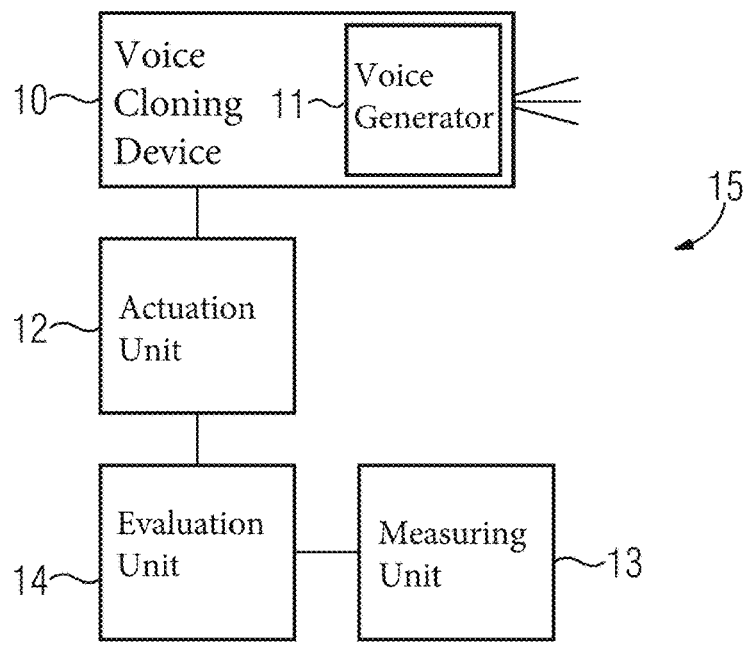

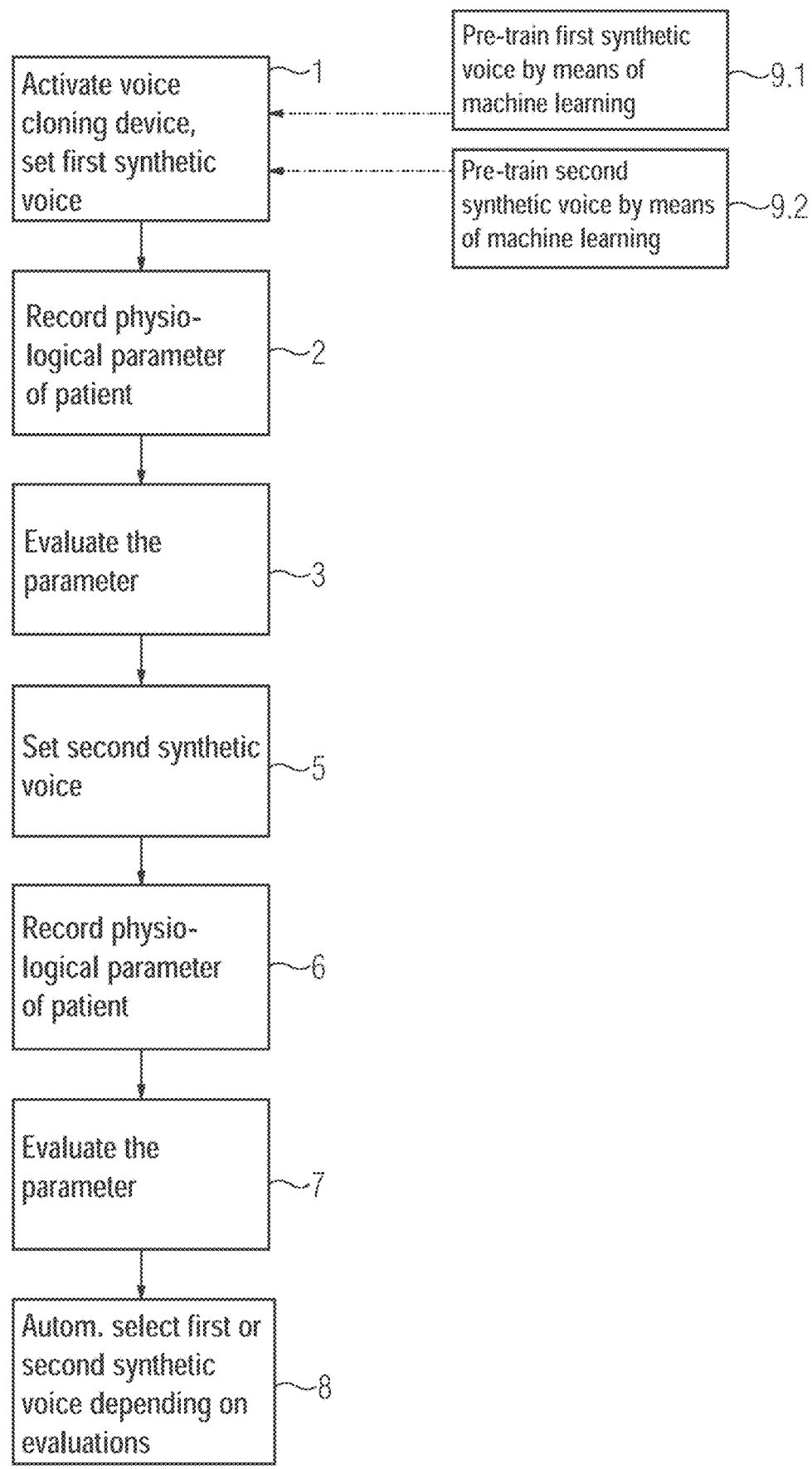

MONITORING SYSTEM FOR MONITORING A PATIENT AND METHOD FOR OPERATING THE MONITORING SYSTEM

This application claims the benefit of German Patent Application No. DE 10 2019 220 224.1, filed on Dec. 19, 2019, which is hereby incorporated by reference in its entirety.

BACKGROUND

The present embodiments relate to monitoring a patient.

When treating patients in medical practices, hospitals or other medical institutions, communication with the patients is an important factor in addition to optimal medical care. Communication with elderly, confused. or dementia patients and with children is particularly difficult. Unsuccessful communication may be medically problematic, for example, in situations such as medical examinations or procedures or operations without general anesthesia. A trusted person or caregiver is often present during preparatory talks prior to examinations or procedures in order to facilitate communication. However, this is no longer the case during examinations, procedures, or operations. Patients often have to communicate directly with the physician, which may be very problematic, especially for the above-mentioned patient group.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a device that allows improved communication with patients, such as young, old, confused, or dementia patients, also during medical procedures is provided. As another example, a method for operating the device is provided.

The present embodiments use voice cloning devices trained to individual speakers. Such devices are generally known, for example, from the online article https://www.vice.com/de/article/3k7mgn/diese-ki-braucht-nur-eine-37-sekunden-lange-aufnahme-dann-klont-sie-eure-stimme or from the article by Arik, Chen et al., "Neural Voice Cloning with a Few Samples," NIPS'18 Proceedings of the 32nd International Conference on Neural Information Processing Systems, pp. 10040-10050, Montréal, Canada, 2018. In another embodiment, the invention uses deepfake devices in an unexpected way. Such devices are known in principle, for example, from the online article https://www.cnet.com/news/samsung-ai-deepfake-can-fabricate-a-video-of-you-from-a-single-photo-mona-lisa-cheapfake-dumbfake/ or from the article by Thies, J. et al.: Face2face: Real-time face capture and reenactment of rgb videos, Proceedings of the IEEE conference on computer vision and pattern recognition, pp. 2387-2395, 2016.

The monitoring system according to the present embodiments for monitoring a patient (e.g., during a medical diagnostic or therapeutic procedure) has a voice cloning device with a voice generator. The cloning device is configured to replace the natural voice of a person (e.g., of medical personnel, such as physicians) with a cloned synthetic voice of another person, where at least two synthetic voices may be selected. The monitoring system also includes a measuring unit that is configured to record at least one physiological parameter of the patient, an evaluation unit that is configured to evaluate the at least one measured physiological parameter of the patient, and an actuation unit that is configured to actuate the voice cloning device such that a synthetic voice is selected or rejected (e.g., for the further operation of the voice cloning device) depending on the result of the evaluation by the evaluation unit. The method according to the present embodiments for operating a monitoring system includes the following acts: activating the voice cloning device, where a first synthetic voice is set; recording at least one physiological parameter of the patient during operation of the voice cloning device with the first synthetic voice; evaluating the at least one physiological parameter of the patient; and automatically actuating the voice cloning device according to the result of the evaluation. For example, depending on the result of the evaluation by the evaluation unit, the first synthetic voice is selected or rejected for further operation of the voice cloning device.

Another variant of a monitoring system according to the present embodiments for monitoring a patient (e.g., during a medical diagnostic or therapeutic procedure) includes a deepfake device with an image generator that is configured to replace the natural visual appearance of a person or the natural environment with a synthetic visual appearance or a synthetic environment that is different from the natural visual appearance of the person or the natural environment. At least two synthetic visual appearances or two synthetic environments may be selected. The monitoring system also includes a visualization device for visualizing the synthetic visual appearance of the person or the surrounding synthetic environment, a measuring unit that is configured to record at least one physiological parameter of the patient, and an evaluation unit that is configured to evaluate the at least one measured physiological parameter of the patient. The monitoring system includes an actuation unit that is configured to actuate the deepfake device such that the synthetic visual appearance or synthetic background is selected or rejected (e.g., for further operation of the deepfake device) depending on the result of the evaluation by the evaluation unit.

If such a device or method is used in a medical setting (e.g., during examinations, procedures, and operations) with patients (e.g., young, elderly, confused or dementia patients), a significant improvement in communication may be achieved. Medical personnel (e.g., physicians performing an operation) may speak to the patient using a synthetic voice (e.g., a voice familiar to the patient such as a relative or acquaintance), thereby achieving better cooperation or producing a calming effect on the patient. Alternatively, medical personnel (e.g., physicians performing an operation) may speak to the patient using a synthetic visual appearance (e.g., someone else's visual appearance such as a face familiar to the patient or the facial expressions or gestures of a relative or acquaintance), thereby achieving better cooperation or having a calming effect on the patient. In this way, dangers that may be caused by a patient becoming anxious may also be avoided. With this device, the calming effect on the patient is provided by measuring and evaluating physiological parameters of the patient and selecting or rejecting the synthetic voice/visual appearance on this basis. Alternatively, it is also possible to simply display a calming synthetic environment, such as a beach or a room familiar to the patient, that is different from the actual environment.

According to an embodiment, the cloned synthetic voices or the synthetic visual appearances/environments have been generated by using a pre-trained algorithm for machine learning. Voice cloning algorithms based on AI are well known, such as a "Deep Voice" algorithm introduced by the Baidu company. These may clone human voices very realistically. Deepfake algorithms based on AI (e.g., algorithms for creating deepfakes, such as inserting different faces in video sequences) are also known. According to another embodiment, pre-training of the algorithm by speech samples or visual appearances of persons known to the patient, especially close ones, has been performed. These persons known to the patient may be, for example, relatives (e.g., parents, children, siblings, spouses, etc.) or acquaintances (e.g., carers, friends) in whom the patient has confidence.

The pre-training of the voice cloning device is carried out using the voice "to be learned" of the corresponding person (e.g., live or by voice samples) in order to learn the characteristics of the voice. After the learning phase, the voice generator of the voice cloning device is able to reproduce sentences spoken by any person (e.g., physician, etc.) in the voice (e.g., synthetic voice) of the person trusted by the patient. For "Deep Voice", for example, only a 3.7 second audio clip is required for training purposes, although longer clips or more examples will naturally give better results. If enough audio material exists, it is also irrelevant whether the person to be voice-cloned is even alive. The age, gender, or accent of the speaker are also irrelevant. For example, known voice cloning algorithms may replace a female voice with a synthetic male voice or a British accent with a US accent.

The pre-training of the deepfake device is performed using photos or video sequences of the corresponding person to learn the characteristics of the person's visual appearance (e.g., face, facial expressions, gestures). After the learning phase, the image generator of the deepfake device is able to reproduce any person (e.g., physician, etc.) in the visual appearance of a person familiar to the patient. This requires optical visualization devices such as monitors or AR/VR headset that the patient is to wear or look into.

According to another embodiment, the evaluation unit is configured to compare at least one measured physiological parameter of the patient with at least one threshold value. This is carried out as part of the evaluation as a simple way of achieving a clear result based on which the synthetic voice or synthetic visual appearance or synthetic environment may be selected or rejected. In this context, the actuation unit is configured to actuate the voice cloning device or the deepfake device such that a synthetic voice or synthetic visual appearance or environment that causes the threshold value to not be exceeded is selected, or a synthetic voice or synthetic visual appearance or environment that causes the threshold value to be exceeded is rejected. If, for example, a physiological parameter of the patient rises well above a threshold value during communication using a particular synthetic voice or synthetic visual appearance or synthetic environment, the synthetic voice or synthetic visual appearance or synthetic environment is rejected, since this is obviously not having a calming effect on the patient. Conversely, if the parameter remains permanently below the threshold value (e.g., if the patient appears calmer), the synthetic voice or synthetic visual appearance or environment will continue to be used. For some parameters, the voice cloning device or deepfake device may also be actuated the opposite way around, so that a synthetic voice or synthetic visual appearance or synthetic environment that causes the threshold value to be exceeded is selected, or a synthetic voice or synthetic visual appearance or synthetic environment that causes the threshold value to be undershot is rejected.

According to another embodiment, the measuring unit is configured to measure a physiological parameter that may be used as an indicator for the state of mind of the patient, and the evaluation unit is configured to evaluate the physiological parameter with respect to the state of mind of the patient. The state of mind of the patient may be the acute mental, psychological, and emotional overall situation of the patient. The physiological parameters used may be constituted by one of the following measurements: blood pressure, pulse, and EEG. Other parameters or a variety of different parameters may also be used. The measuring unit may contain sensors, cameras, or other transducers.

According to another embodiment, the actuation unit is configured to actuate the voice cloning device or deepfake device such that a synthetic voice or synthetic visual appearance or synthetic environment that produces a positive state of mind is selected, or a synthetic voice or synthetic visual appearance or synthetic environment that produces a negative state of mind is rejected. A positive state of mind may be a state of mind in which the patient is calm and/or cooperative and/or feels comfortable. A negative state of mind may be a state of mind in which the patient is stressed, restless, or anxious.

According to further embodiments, the evaluation of at least one physiological parameter of the patient includes a comparison with at least one threshold value and/or an evaluation with respect to the patient's state of mind.

The device may be actuated such that the first synthetic voice or first synthetic visual appearance or first synthetic environment is selected if the evaluation of the at least one physiological parameter shows that a threshold value for the parameter is not exceeded, and the first synthetic voice or first synthetic visual appearance or first synthetic environment is rejected if evaluation of the at least one physiological parameter shows that a threshold value for the parameter is exceeded. In addition, the device may be actuated such that the first synthetic voice or first synthetic visual appearance or first synthetic environment is selected if the first synthetic voice or first synthetic visual appearance or first synthetic environment produces a positive state of mind in the patient, and that the first synthetic voice or first synthetic visual appearance or first synthetic environment is rejected if the first synthetic voice or first synthetic visual appearance or first synthetic environment causes a negative state of mind.

According to another embodiment, at least one physiological parameter is measured and evaluated for at least one second synthetic voice (in addition to the first synthetic voice) in each case, and, depending on the evaluation of the physiological parameter, a synthetic voice is selected from the selection of the first synthetic voice and the at least second synthetic voice for further operation of the voice cloning device. Thus, at least two synthetic voices are tested with respect to effect (e.g., calming effect) on the patient. The synthetic voice that produces the more positive state of mind in the patient or best helps to calm the patient is then selected.

Alternatively, at least one physiological parameter is measured and evaluated for at least a second synthetic visual appearance or a second synthetic environment, and, depending on the evaluation of the physiological parameter, a synthetic visual appearance or synthetic environment is selected from the selection of the first synthetic visual appearance and the at least second synthetic visual appearance or the first synthetic environment and the at least second synthetic environment for the further operation of the deepfake device.

BRIEF DESCRIPTION OF THE DRAWINGS

FIG. 1 shows a flowchart of the basic acts of one embodiment of a method;

FIG. 2 shows a view of one embodiment of a device; and

FIG. 3 shows another embodiment of the method with additional acts.

DETAILED DESCRIPTION

Particularly in situations such as medical examinations or procedures or operations without general anesthesia, the purpose of the present embodiments is to improve communications, especially with elderly, confused, or dementia patients and also with children, using voice cloning systems or deepfake devices via which the physicians may communicate with the patients using the voices of reference persons (e.g., synthetic voices) or the faces, facial expressions, or gestures of reference persons (e.g., synthetic visual appearance) in order to achieve better cooperation and/or to be able to produce a calming effect.

FIG. 1 shows basic steps of the method according to the present embodiments, using the example of a voice cloning device. These acts are performed by a monitoring system 15 as shown in FIG. 2. The method is used, for example, for communication between a physician A and a patient P. In a first act 1, a voice cloning device 10 of the monitoring system 15 is activated, where a first synthetic voice F1 is set. The first synthetic voice F1 has, as will be described later, been previously cloned (e.g., by a machine learning algorithm) and represents the voice of a person known or trusted by the patient P. For example, the synthetic voice F1 may be the voice of the husband/wife of the patient P, a child of the patient P, a friend or relative of the patient P, a parent of the patient P, or a caregiver of the patient P. If the voice cloning device 10 is activated, the incorporated voice generator 11 provides that the original voice of the physician A is replaced by the cloned synthetic voice F1 (e.g., that the spoken word of the physician A is simultaneously replaced by the synthetic voice F1). The voice cloning device 10 has at least two cloned synthetic voices to choose from (e.g., the first synthetic voice F1 and a second synthetic voice F2). Preselection and setting may be performed both automatically and manually.

In a second act 2, at least one physiological parameter of the patient is recorded or measured during operation of the voice cloning device using the first synthetic voice. This is takes place by a measuring unit 13 assigned to the monitoring system 15. The measuring unit 13 has, for example, one or more sensors, cameras, or other transducers or is constituted by one of these. The at least one physiological parameter may be used, for example, as an indicator of the patient's state of mind. The at least one physiological parameter may be constituted, for example, by blood pressure, pulse, or EEG, where, for example, pulse sensors, EEG electrodes, or blood pressure sensors may be used. It is also possible to measure any other physiological parameters that may indicate the state of mind or the condition of the patient P. The physiological parameter(s) may be measured once or over a previously set period of time. In a third act 3, the at least one physiological parameter of the patient is evaluated by an evaluation unit 14 assigned to the monitoring system 15. This evaluation may simply involve, for example, a comparison with one or more threshold values or a more complex analysis regarding a positive or negative state of mind of the patient.

After the evaluation, in a fourth act 4, the voice cloning device 10 is automatically actuated by an actuation unit 12 assigned to the monitoring system 15 as a function of the result of the evaluation. For example, the first synthetic voice F1 is retained or selected if the evaluation shows a positive effect of the first synthetic voice F1 on the patient P (e.g., if the patient's state of mind is or becomes positive, if the patient is or becomes calmer or cooperates better than before). In the simplest case, the first synthetic voice F1 is retained or selected, provided that the parameter does not exceed a threshold value (e.g., pulse, blood pressure, etc.). The first synthetic voice F1 is rejected or terminated if the evaluation shows a negative effect of the first synthetic voice F1 on the patient P (e.g., if the patient's state of mind is or becomes negative, if the patient is or becomes agitated, anxious, or disturbed, if the patient shows symptoms of stress, or if the patient's willingness to cooperate decreases). In the simplest case, the first synthetic voice F1 is rejected or terminated if the evaluation indicates that the threshold value(s) has been exceeded.

FIG. 3 shows an expanded embodiment. After the first synthetic voice F1 is set in the first act 1, at least one physiological parameter is measured in a second act 2 and evaluated in a third act 3; then, in a fifth act 5, a further second synthetic voice F2 is activated so that, for example, the physician A now speaks using the second synthetic voice F2. Then, in a sixth act 6, at least one physiological parameter of the patient is likewise recorded or measured by the measuring unit 13 (e.g., the same physiological parameter(s) as in the case of the first synthetic voice F1 in order to provide comparability). Then, in a seventh act 7, the measured parameters are evaluated by the evaluation unit. The evaluation may be performed in a comparable manner to the evaluation when using the first synthetic voice F1 (e.g., simply by comparison with one or more threshold values or in a more complex manner with regard to a positive or negative state of mind of the patient).

In an eighth act 8, depending on the evaluation, the synthetic voice with the most positive effect on the patient P is then automatically selected from the two synthetic voices. More than two synthetic voices may be used (e.g., three or four synthetic voices).

In a preliminary process, the synthetic voices may be cloned by machine learning. This may be carried out, for example, using audio recordings of the voices to be cloned. It is possible to clone the voices of living persons or also the voices of already deceased persons; for this purpose, merely audio recordings (e.g., film, sound recordings, answering machines, etc.) of sufficient length are necessary. Prior to using the actual method, the first synthetic voice was cloned in a ninth act 9.1, and the second synthetic voice was cloned in a tenth act 9.2 in FIG. 3. This may be performed immediately before or even some time (e.g., days, weeks, etc.) before using the actual method. In general, methods for creating cloned voices are well known (see e.g., as explained above).

The general method may be used in a medical environment (e.g., for examinations, procedures, and operations without general anesthesia), but may also be used in other environments, such as nursing homes. The method may be performed during the described situations or in advance to prepare for the corresponding situation. The synthetic voice selected there may then be used by the monitoring system 15 in the medical environment.

Provision may also be made for selecting different synthetic voices for different situations. For example, for this purpose, results (e.g., objective results; that the patient follows instructions) may also be included in the evaluations and may be taken into account for selecting or rejecting a synthetic voice. In this context, individual situations are tested using each synthetic voice (e.g., following instructions such as breathing commands and remaining calm). It may happen that a different synthetic voice is more suitable in each situation (e.g., the first synthetic voice is suitable for calming, and the second synthetic voice is suitable for the following of instructions). This may be learned by the monitoring system 15 (e.g., by machine learning) so that the monitoring system 15 then sets the most suitable synthetic voice according to the evaluation of the respective situations by the actuation unit.

The method described in FIGS. 1 and 3 may also be transferred directly to a deepfake device and may be executed in the same way.

With deepfake methods (e.g., a portmanteau of "deep learning" and "fake"), media content (e.g., videos) may be modified and falsified largely autonomously by artificial intelligence techniques. The resulting fake videos are largely realistic and difficult to distinguish from an original. Deepfake offers various possibilities: "face swapping", where the face of one person is swapped with a generated face of another person in videos or photos. Alternatively, the environment of the video may be swapped so that people are placed in a new context. Another application is the transfer of body movements to other persons in video material, known as "body puppetry".

Virtual reality (VR) is the representation and simultaneous perception of reality and corresponding physical properties in a real-time computer-generated, interactive virtual environment. A mixing of virtual reality and physical reality is referred to as mixed or augmented reality (AR).

With regard to the AR/VR visualization devices used, there are two categories that may be used within the scope of the present embodiments (e.g., to make synthetic visual appearances or synthetic environments visible to the patient, so-called optical see-through devices such as HoloLens2 in which virtual objects are additionally superimposed on the environment via optical lenses, or video see-through devices such as Varjo XR1 that are based on VR headsets but also feed video signals into the headset from outside).

Optical see-through devices are small and portable, but limited in the size of the visible area and may only partially "mask out" real objects. Video see-through devices create a complete mask-out and have a large visible range, but are often large, heavy, and typically also hard-wired.

Within the scope of the method according to the present embodiments, the patient wears one of the visualization devices described (e.g., AR headset, VR headset, HoloLens) or looks into one (e.g., screen).

The method is used, for example, for communication between a physician A and a patient P. First, a deepfake device of the monitoring system is activated, where a first synthetic visual appearance (e.g., "animated avatar") is set. As will be described later, the first synthetic visual appearance has been previously generated by a machine learning algorithm and represents the face, facial expressions, or gestures of a person known to or trusted by the patient P (e.g., husband/wife, child, friend or relative, parent, or caregiver). If the deepfake device is activated, the incorporated image generator provides that the original visual appearance of the physician A is replaced by the cloned synthetic visual appearance.

The deepfake device has at least two cloned synthetic visual appearances from which to choose. These may be pre-selected and set automatically or manually. At least one physiological parameter of the patient is then recorded or measured during operation of the deepfake device. This is performed by a measuring unit 13 that is assigned to the monitoring system 15 and has, for example, one or more sensors, cameras, or other sensing elements or is constituted by one of these. The at least one physiological parameter may be used, for example, as an indicator of the patient's state of mind. The at least one physiological parameter may be constituted, for example, by one of the following measured values: blood pressure, pulse, and EEG. For example, pulse sensors, EEG electrodes, or blood pressure sensors may be used for this purpose. It is also possible to measure any other physiological parameters that are indicative of the state of mind or condition of the patient P. The physiological parameter(s) may be measured once or over a previously selected period of time. The at least one physiological parameter of the patient is then evaluated by an evaluation unit assigned to the monitoring system. The evaluation may, for example, simply include a comparison with one or more threshold values or involve a more complex evaluation with respect to a positive or negative state of mind of the patient.

Following the evaluation, the deepfake device is automatically actuated by an actuation unit 12 assigned to the monitoring system 15 according to the result of the evaluation. For example, the first synthetic visual appearance is retained or selected if the evaluation shows a positive effect on the patient P (e.g., if the patient's state of mind is or becomes positive, if the patient is or becomes calmer or more cooperative than before). In the simplest case, the first synthetic visual appearance is retained or selected if the parameter does not exceed a threshold value (e.g., pulse, blood pressure, etc.). The first synthetic visual appearance is rejected or terminated if the evaluation indicates a negative effect on the patient P (e.g., if the patient's state of mind is or becomes negative, if the patient becomes agitated, anxious, or disturbed, if the patient shows symptoms of stress or if the patient's willingness to cooperate decreases). In the simplest case, the first synthetic visual appearance is discarded or terminated if the evaluation shows that the threshold value(s) has/have been exceeded.

In an expanded embodiment, a further, second synthetic visual appearance may then be activated. Then, in a sixth act 6, at least one physiological parameter of the patient is also recorded or measured by the measuring unit 13 (e.g., the same physiological parameter(s) in order to provide comparability). The measured parameters are then evaluated by the evaluation unit. The evaluation may be carried out in a comparable manner to the previous evaluation (e.g., simply by comparison with one or more threshold values or, with greater complexity, with respect to a positive or negative state of mind of the patient). Subsequently, depending on the evaluation, the synthetic visual appearance that has the most positive effect on the patient P with regard to the patient's state of mind is automatically selected. Self-evidently, more than two (e.g., three or four synthetic visual appearances) may also be used.

As part of the method, the scenery may be recorded from the patient's point of view (e.g., typically using RGB or RGB-D cameras). Alternatively or in addition, various other room cameras may be used. In the video recordings, the OR staff are selectively replaced by "more comfortable faces" (e.g., avatars) using deepfake algorithms, and the patient is presented with the altered images live via the AR/VR visualization device worn by the patient (e.g., AR headset, VR headset, HoloLens, screen). For example, face masks may also be eliminated, making the situation much more pleasant for the patient. Also, calming emotions and facial expressions that were otherwise not visible may be made visible to the patient. During the intervention, the physician may now speak to the patient as one of the previously trained reference persons in the form of an avatar. In addition, the environment within the operating room may be transformed, which also has a calming effect on the patient. For example, the scenery may be relocated virtually to a Caribbean beach, a sunbathing lawn, or into the patient's own living room or bedroom.

In the course of the intervention or in a trial conversation with the patient, the system is able to "learn" which avatar was successful in which situation (e.g., by determining the success of an instruction). The system may then independently use avatar X for "calming actions", avatar Y for instructions, etc. Learning may also take place pre-operatively using test sequences.

The present embodiments may be briefly summarized as follows: for particularly good communication even with difficult patients, a monitoring system for monitoring a patient, especially during a medical diagnostic or therapeutic procedure, is provided. The monitoring system includes a voice cloning device with a voice generator that is configured to replace a natural voice of a person with a cloned synthetic voice different from the voice of the person, where at least two synthetic voices may be selected. The monitoring system also includes a measuring unit that is configured to record at least one physiological parameter of the patient, an evaluation unit that is configured to evaluate the at least one measured physiological parameter of the patient, and an actuation unit that is configured to actuate the voice cloning device such that a synthetic voice is selected or rejected (e.g., for the further operation of the voice cloning device) depending on the result of the evaluation by the evaluation unit.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A monitoring system for monitoring a patient, the monitoring system comprising:
   a voice cloning device including a voice generator, the voice cloning device being configured to:
   replace a natural voice of a person with a first cloned synthetic voice different from the natural voice of the person, the first cloned synthetic voice being selectable from at least two cloned synthetic voices; and
   output the first cloned synthetic voice;
   a measuring unit configured to record at least one physiological parameter of the patient during operation of the voice cloning device using the first cloned synthetic voice;
   an evaluation unit configured to evaluate the at least one physiological parameter of the patient; and
   an actuation unit configured to actuate the voice cloning device such that the first cloned synthetic voice is selected or rejected depending on a result of the evaluation of the at least one physiological parameter of the patient by the evaluation unit,
   wherein the evaluation of the at least one physiological parameter of the patient comprises comparison of the at least one physiological parameter with at least one threshold value, and
   wherein the actuation of the voice cloning device takes place such that the first cloned synthetic voice is selected when the evaluation of the at least one physiological parameter indicates that a threshold value of the at least one threshold value for the at least one physiological parameter is not exceeded, and that the first cloned synthetic voice is rejected when the evaluation of the at least one physiological parameter indicates that a threshold value for the at least one physiological parameter is exceeded.

2. The monitoring system of claim 1, wherein the actuation unit is further configured to actuate the voice cloning device such that a second cloned synthetic voice of the at least two cloned synthetic voices that does not cause the threshold value to be exceeded is selected or a third cloned synthetic voice of the at least two cloned synthetic voices that causes the threshold value to be exceeded is rejected.

3. The monitoring system of claim 1, wherein the first cloned synthetic voice has been generated using a pre-trained algorithm for machine learning.

4. The monitoring system of claim 3, wherein pre-training of the algorithm was carried out by speech samples of persons known to the patient.

5. The monitoring system of claim 1, wherein the measuring unit is further configured to measure a physiological parameter that is usable as an indicator for a state of mind of the patient, and
   wherein the evaluation unit is further configured to evaluate the physiological parameter with respect to the state of mind of the patient.

6. The monitoring system of claim 1, wherein the at least one physiological parameter is constituted by blood pressure, pulse, or EEG.

7. The monitoring system of claim 1, wherein the actuation unit is further configured to actuate the voice cloning device such that a second cloned synthetic voice of the least two cloned synthetic voices that produces a positive state of mind is selected or a third cloned synthetic voice of the least two cloned synthetic voices that produces a negative state of mind is rejected.

8. A method for operating a monitoring system for monitoring a patient, the monitoring system comprising a voice cloning device, the voice cloning device including a voice generator and being configured to replace a natural voice of a person with a first cloned synthetic voice different from the natural voice of the person, and output the first cloned synthetic voice, the method comprising:
   activating the voice cloning device, wherein the first synthetic voice is set;
   recording, by a measuring unit of the monitoring system, at least one physiological parameter of the patient during operation of the voice cloning device using the first synthetic voice;
   evaluating, by an evaluation unit of the monitoring system, the at least one physiological parameter of the patient for the first synthetic voice;

automatically actuating, by an actuation unit of the monitoring system, the voice cloning device depending on a result of the evaluating of the at least one physiological parameter of the patient;

measuring and evaluating at least one physiological parameter for at least one second synthetic voice; and depending on the evaluating of the at least one physiological parameter for the at least one second synthetic voice, selecting a synthetic voice from the first synthetic voice and the at least one second synthetic voice for further operation of the voice cloning device.

9. The method of claim 8, wherein, depending on the result of the evaluating by the evaluation unit, the first synthetic voice is selected or rejected for further operation of the voice cloning device.

10. The method of claim 8, wherein evaluating the at least one physiological parameter of the patient comprises comparing the at least one physiological parameter with at least one threshold value.

11. The method of claim 10, wherein activating the voice cloning device takes place such that the first synthetic voice is selected when the evaluating of the at least one physiological parameter indicates that a threshold value for the at least one physiological parameter is not exceeded, and that the first synthetic voice is rejected when the evaluating of the at least one physiological parameter indicates that a threshold value for the at least one physiological parameter is exceeded.

12. The method of claim 8, wherein evaluating the at least one physiological parameter comprises evaluating the at least one physiological parameter with respect to a state of mind of the patient.

13. The method of claim 12, wherein activating the voice cloning device takes place such that the first synthetic voice is selected when the first synthetic voice produces a positive state of mind in the patient, and that the first synthetic voice is rejected when the first synthetic voice produces a negative state of mind.

14. The method of claim 12, wherein the synthetic voice that produces a most positive state of mind in the patient is selected.

15. A method for operating a monitoring system for monitoring a patient, the method comprising:

activating a voice cloning device of the monitoring system, such that a first synthetic voice is set, the voice cloning device comprising a voice generator and being configured to replace a natural voice of a person with the first synthetic voice, which is different than the natural voice of the person, and output the first synthetic voice, the first synthetic voice being selectable from at least two synthetic voices;

recording, by a measuring unit of the monitoring system, the at least one physiological parameter of the patient during operation of the voice cloning device using the first synthetic voice;

evaluating, by an evaluation unit of the monitoring system, the at least one physiological parameter of the patient; and automatically actuating, by an actuation unit of the monitoring system, the voice cloning device depending on a result of the evaluating, wherein evaluating the at least one physiological parameter of the patient comprises comparing the at least one physiological parameter with at least one threshold value, and wherein activating the voice cloning device takes place such that the first synthetic voice is selected when the evaluating of the at least one physiological parameter indicates that a threshold value of the at least one threshold value for the at least one physiological parameter is not exceeded, and that the first synthetic voice is rejected when the evaluating of the at least one physiological parameter indicates that the threshold value for the at least one physiological parameter is exceeded.

* * * * *